(12) United States Patent
Heinecke et al.

(10) Patent No.: US 6,685,682 B1
(45) Date of Patent: Feb. 3, 2004

(54) CARRIER DELIVERED DRESSING AND METHOD OF MANUFACTURE

(75) Inventors: Steven B. Heinecke, New Richmond, WI (US); Donald G. Peterson, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/427,245

(22) Filed: Oct. 26, 1999

Related U.S. Application Data

(60) Division of application No. 09/010,104, filed on Jan. 21, 1998, now Pat. No. 6,169,224, which is a continuation of application No. 08/463,788, filed on Jun. 5, 1995, now Pat. No. 5,738,642, which is a division of application No. 08/258,789, filed on Jun. 13, 1994, now Pat. No. 5,531,855, which is a continuation-in-part of application No. 08/034,306, filed on Mar. 22, 1993, now abandoned.

(51) Int. Cl.⁷ .................. A61F 13/02; A61F 13/00; A61M 13/00
(52) U.S. Cl. .................. 604/307; 604/304; 604/308; 604/58; 602/41; 602/43; 602/54; 602/57; 602/904
(58) Field of Search .................. 604/304–8, 180, 604/58; 602/43, 52, 54, 56, 58, 41, 42, 57, 900, 904; 206/440, 438, 441; 128/849, 853, 854, 887, 888; 428/40.1, 41.7, 41.8, 292.1, 304.4, 411.1

(56) References Cited

U.S. PATENT DOCUMENTS

| | | | |
|---|---|---|---|
| 2,532,011 A | 11/1950 | Dahlquist et al. | 154/53.5 |
| 2,785,677 A | 3/1957 | Stumpf | 128/156 |
| RE24,906 E | 12/1960 | Ulrich | 206/59 |

(List continued on next page.)

FOREIGN PATENT DOCUMENTS

| | | | |
|---|---|---|---|
| CA | 659528 | 3/1963 | |
| EP | 0 051 935 A2 | 5/1982 | |
| EP | 0 066 899 A2 | 12/1982 | |
| EP | 0 081 990 A1 | 5/1983 | |
| EP | 0 090 564 A3 | 10/1983 | |
| EP | 0 101 298 | 2/1984 | ........... A61F/13/02 |
| EP | 0 236 104 A3 | 9/1987 | |
| EP | 0 465 023 A1 | 1/1992 | |
| EP | 0 541 251 A1 | 5/1993 | |
| GB | 2 120 104 A | 11/1983 | |
| GB | 2 131 299 A | 6/1984 | |
| JP | 59-214449 | 12/1984 | |

OTHER PUBLICATIONS

Brochure "Wound Care", 3M Health Care, 70–2008–4526–4.
Brochure "3M Tegasorb™ Thin hydrocolloid dressing", 3M Health Care, 70–2008–6475–2.
Brochure "3M Tegasorb™", 3M Medical–Surgical Division, 34–7029–9322.
Brochure "3M Tegaderm Transparent Dressin", 3M Health Care, 70–2008–7408–2.
Brochure "3M Tegaderm™ 1624W transparent dressing", 3M Health Care, 70–2008–6769–8.

(List continued on next page.)

*Primary Examiner*—Patricia Bianco
(74) *Attorney, Agent, or Firm*—Nancy M. Lambert

(57) ABSTRACT

A carrier delivered dressing which has a conformable backing with a pressure sensitive adhesive coated on a bottom face and a low adhesion coating on a top face. The backing is supported during shipping and handling by a liner attached to the adhesive and a removable heat sealed carrier attached to the top face of the backing. The method according to the present invention discloses the steps of forming and optionally removing windows in a carrier material and nonpermanently heat sealing the carrier to the backing to form the dressings of the present invention.

11 Claims, 7 Drawing Sheets

U.S. PATENT DOCUMENTS

| | | | |
|---|---|---|---|
| 3,020,186 A | 2/1962 | Lawrence | 156/248 |
| 3,329,548 A | 7/1967 | Blatz | 156/251 |
| 3,389,827 A | 6/1968 | Abere et al. | 220/53 |
| 3,645,835 A | 2/1972 | Hodgson | 161/146 |
| 4,112,213 A | 9/1978 | Waldman | 526/279 |
| 4,310,509 A | 1/1982 | Berglund et al. | 424/28 |
| 4,323,557 A | 4/1982 | Rosso et al. | 424/28 |
| 4,328,057 A | 5/1982 | Gutow | 156/248 |
| 4,374,520 A | 2/1983 | Grossmann et al. | 128/132 |
| 4,413,621 A | 11/1983 | McCracken et al. | 128/156 |
| 4,472,480 A | 9/1984 | Olson | 428/332 |
| 4,485,809 A | 12/1984 | Dellas | 128/156 |
| 4,499,896 A | 2/1985 | Heinecke | 128/156 |
| 4,524,095 A | 6/1985 | Gocket et al. | 428/43 |
| 4,545,371 A | 10/1985 | Grossmann et al. | 128/132 |
| 4,549,063 A | 10/1985 | Ang et al. | 219/121 |
| 4,587,146 A | 5/1986 | Anhauser et al. | 428/41 |
| 4,588,400 A | 5/1986 | Ring et al. | 604/304 |
| 4,590,022 A | 5/1986 | Cloca et al. | 264/41 |
| 4,595,001 A | 6/1986 | Potter et al. | 128/156 |
| 4,595,011 A | 6/1986 | Phillips | 128/636 |
| 4,596,738 A | 6/1986 | Metcalfe et al. | 428/308 |
| 4,600,001 A | 7/1986 | Gilman | 128/156 |
| 4,614,183 A | 9/1986 | McCracken et al. | 128/132 |
| 4,638,043 A | 1/1987 | Szycher et al. | 528/75 |
| 4,664,106 A | 5/1987 | Snedeker | 128/156 |
| 4,678,462 A | 7/1987 | Vaillancourt | 604/180 |
| 4,706,662 A | 11/1987 | Thompson | 128/155 |
| 4,728,323 A | 3/1988 | Matson | 604/304 |
| 4,737,410 A | 4/1988 | Kantner | 428/343 |
| 4,753,232 A | 6/1988 | Ward | 128/156 |
| 4,787,380 A | 11/1988 | Scott | 128/156 |
| 4,808,172 A | 2/1989 | Murata | 604/306 |
| 4,915,102 A | 4/1990 | Kwiatek et al. | 128/156 |
| 4,917,112 A | 4/1990 | Kalt | 128/156 |
| 4,941,882 A | 7/1990 | Ward et al. | 604/180 |
| RE33,353 E | 9/1990 | Heinecke | 428/40 |
| 4,967,740 A | 11/1990 | Riedel | 128/156 |
| 5,018,516 A | 5/1991 | Gilman | 128/155 |
| RE33,727 E | 10/1991 | Sims | 128/85 |
| 5,064,422 A | 11/1991 | Wick | 604/307 |
| 5,088,483 A | 2/1992 | Heinecke | 602/46 |
| 5,092,323 A | 3/1992 | Riedel et al. | 602/54 |
| 5,106,383 A | 4/1992 | Mulder et al. | 604/389 |
| 5,106,629 A | 4/1992 | Cartmell et al. | 424/445 |
| 5,160,315 A | 11/1992 | Heinecke et al. | 602/57 |
| 5,197,493 A | 3/1993 | Grier-Idris | 128/853 |
| 5,259,835 A | 11/1993 | Clark et al. | 602/48 |
| 5,336,162 A | 8/1994 | Ota et al. | 602/41 |
| 5,520,629 A | 5/1996 | Heinecke et al. | 602/57 |
| 5,531,855 A | 7/1996 | Heinecke et al. | 156/252 |
| 5,738,642 A | 4/1998 | Heinecke et al. | 602/58 |
| 5,891,078 A | 4/1999 | Turngren et al. | 602/58 |
| 5,899,871 A | 5/1999 | Cartmell et al. | 602/43 |

OTHER PUBLICATIONS

Brochure "3M Tegasorb™ ulcer dressing", 3M Health Care, 70–2008–4530–6.

Brochure "Tegasorb™ Ulcer Dressing", 3M Health Care, 70–2008–2728–8.

Brochure "Tegaderm™ Transparent Dressing", 3M Health Care, 70–2008–5413–4.

"Handbook of Pressure–Sensitive Adhesive Technology", Chapter 18, pp. 384–403, Van Nostrand Reinhold Company, 1982.

FIG. 5B
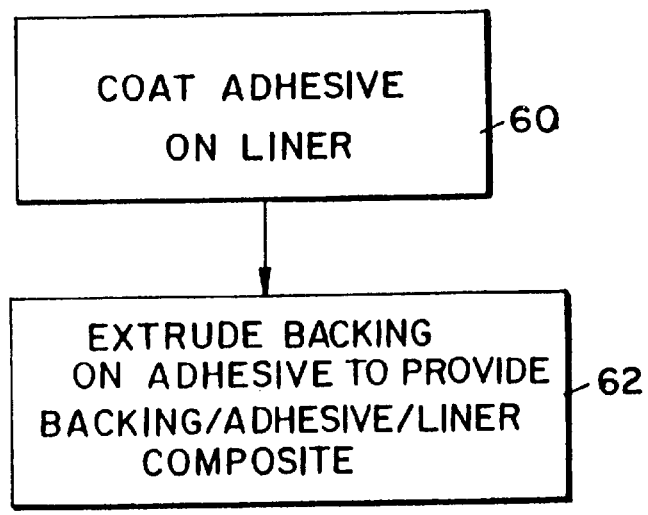
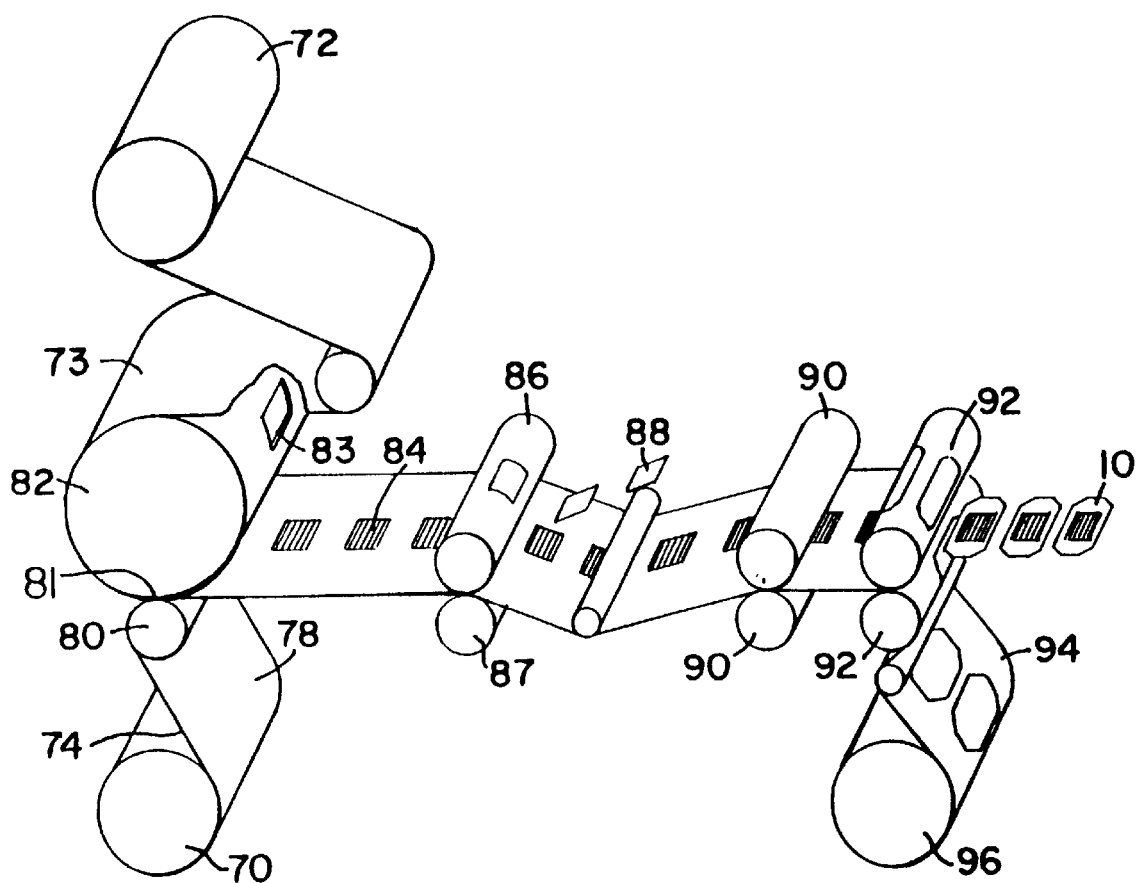
FIG. 6

CARRIER DELIVERED DRESSING AND METHOD OF MANUFACTURE

RELATED APPLICATIONS

This is a divisional of application Ser. No. 09/010,104, filed Jan. 21, 1998, U.S. Pat. No. 6,169,224 B1, which is a continuation of application Ser. No. 08/463,788, filed Jun. 5, 1995, U.S. Pat. No. 5,738,642, which is a divisional of application Ser. No. 08/258,789, filed Jun. 13, 1994, U.S. Pat. No. 5,531,855, which is a continuation-in-part of application Ser. No. 08/034,306, filed Mar. 22, 1993, abandon.

FIELD OF THE INVENTION

The present invention relates to pressure sensitive adhesive composite dressings comprising thin film backings coated on one side with a pressure sensitive adhesive, that are delivered by a removable carrier. The present invention also relates to methods of manufacturing such pressure sensitive adhesive composite dressings.

BACKGROUND OF THE INVENTION

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), OP-SITE™ (T. J. Smith & Nephew, Hull, England), and UNIFLEX™ (How Medica, Largo, Fla.).

The polymeric films used in those dressings and drapes, referred to as dressings below, are conformable, i.e., the films are extremely thin, flexible and supple. They are typically supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem.

One known delivery system is described in U.S. Pat. No. 4,485,809 in which a dressing is attached to a release liner by the use of adhesive between the dressing and the liner. The liner material functions as a frame to provide support during placement of the dressing after a center section of the release liner has been removed. After the dressing has been affixed, the frame is removed from the dressing by tearing the film along perforations provided around the center section. Because the center section functions as a liner, however, it cannot be removed until immediately before the dressing is placed on a patient. Furthermore, because the frame must be torn from the perimeter of the dressing, the adhesive bond between the skin and the dressing is often disturbed, which can then lead to premature failure and removal of the dressing by bed linens and other means.

U.S. Pat. No. 4,600,001 also describes a delivery system which includes a pair of opposed strips and a delivery layer which is heat laminated to the film. In use, a release liner is removed from a dressing, the dressing is placed on a patient, the delivery means layer is then removed from attachment with the film. After the film is secured on a patient, the opposed strips and film attached to them are removed using perforations in the film. In this device, the delivery means layer is preferably transparent or translucent to allow viewing through the dressing during placement. Like the dressing described above, the tearing of the film to remove the opposed strips can disturb the adhesive bond between the skin and the dressing, again leading to premature failure.

Carrier-type delivery systems offer an alternative delivery system for use with conformable thin films. The use of a removable carrier, which does not require tearing of the film after it has been placed on the patient, avoids the problems described above. Furthermore, a center portion of the carrier is preferably removable thus forming a frame which allows one to view the attachment site on a patient through the film exposed within the frame. The frame-type carrier aids in accurate placement of the dressing on a patient.

EPO Publication No. 0 051 935 describes a removable frame delivery system for thin polymeric film dressings. In that delivery system, the bond between the frame material and the film is mechanical in nature and is formed when the film is extruded onto the frame material. Dressings according to this reference are manufactured with a central window which is control depth die cut in the frame material. In use, the die cut window is first removed from the center of the frame, after which the release liner is removed from the adhesive layer and the dressing is placed on a patient. The frame is then removed from the film leaving the dressing in place on the patient.

One drawback associated with dressings manufactured according to EPO Publication No. 0 051 935 is the limited amount of control a manufacturer may exercise over the strength of an extruded or mechanical bond. To facilitate placement of the dressing, EPO Publication No. 0051935 teaches that the tenacity of the bond between the film and the frame material must be greater than the tenacity of the bond between the film and the liner. Extruding allows a manufacturer limited control over the tenacity of a bond.

U.S. Pat. No. Re 33,727 also describes a frame type delivery system including a composite with a thin polymeric film and a pressure-sensitive adhesive coated on one surface of the polymeric film. A release liner is attached to the adhesive coated surface of the film and a frame is attached to the exposed surface of the film opposite the surface to which the adhesive has been applied. When applied, the release liner is first removed from the adhesive coated surface, the film and frame are then placed on a patient and the frame is then removed from the film, which is left on the skin.

U.S. Pat. No. Re 33,727 does not discuss the mechanism by which the frame is bonded to the film, nor does it discuss the problems associated with removing the central window without disturbing the bond between the frame and the film. The patentee in Re 33,727, however, relied on label construction for enablement which used either pressure sensitive adhesives or a radiation-curable film to bond layers of a composite together. In this regard, such frame delivered dressings according to the above references contemplate the extrusion or radiation curing of the thin film directly on the carrier material.

A low adhesion coating on the top face of the dressing provides the ability to apply and remove tapes and other devices over the dressing, thereby enabling the dressing to be used as a platform for those tapes and other devices. The low adhesion coating allows the tapes and other devices to be removed without also removing or disturbing the underlying dressing and allowing additional contamination to reach the wound. An example of such a dressing is TEGADERM™ No. 1620 dressing available from 3M Company, St. Paul, Minn.

SUMMARY OF THE INVENTION

The adhesive composite and methods of manufacturing the same of the present invention address the above-noted problems by providing a carrier delivered dressing having a conformable backing with a pressure sensitive adhesive coated on a bottom face and an optional low adhesion coating on a top face, and which is supported by a removable carrier attached to the top face of the backing. In particular, the present invention overcomes the problems discussed above by heat sealing the carrier to the top face of the backing, and optionally over a heat seal compatible low adhesion coating on the top face of the backing. Furthermore, in one embodiment, the method and apparatus of the present invention provide such a carrier delivered dressing in which the window is optionally removed prior to use by the consumer, thereby minimizing the steps necessary to apply the dressings and reducing the waste stream at the consumer level.

In one preferred method, the present invention also offers the advantage of a reduced number of processing steps which, in turn, further reduces the costs associated with producing dressings according to the present invention. Furthermore, in one embodiment the application of a low adhesion coating on the backing which is compatible with the heat seal bond between the carrier and the backing provides a product, displaying reduced friction between the dressing and bed linens. This results in less accidental removal of the dressings reducing potential contamination of the wound.

In particular, the present invention provides an adhesive composite dressing comprising: (a) a conformable backing having top and bottom faces; (b) a pressure sensitive adhesive coated on at least a portion of the bottom face of the backing; (c) a liner releasably adhered to the pressure sensitive adhesive opposite the backing; and (d) a carrier releasably attached to and covering at least a portion of the top face of the low adhesion coating and backing, the carrier being nonpermanently heat-sealed to the low adhesion coating and backing and a cut in the carrier substantially defining a window proximate a center of the carrier, the carrier further being formed of material substantially more rigid than the backing to provide rigidity to the adhesive composite. The composite dressing may also include an optional low adhesion coating on the top face of the backing, in between the carrier and the top face of the backing.

The present invention also provides a method of manufacturing an adhesive composite dressing comprising the steps of: (a) providing a conformable backing having top and bottom faces, a pressure sensitive adhesive on at least a portion of the bottom face of the backing and a liner on the pressure sensitive adhesive; (b) non-permanently heat sealing a carrier to the top face of the backing, the bond between the carrier and top face of the backing being greater than the bond between the liner and the pressure sensitive adhesive; the carrier having a cut defining a window proximate a center of the carrier.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying drawings wherein:

FIGS. 5A & 5B are flow charts of alternate preferred methods of providing backing/pressure sensitive adhesive/liner composites during a preferred manufacturing process according to the present invention;

FIG. 6 is a schematic diagram in perspective of one preferred method of manufacturing dressings according to the present invention;

DETAILED DESCRIPTION OF EMBODIMENTS OF THE INVENTION

Figure 1:
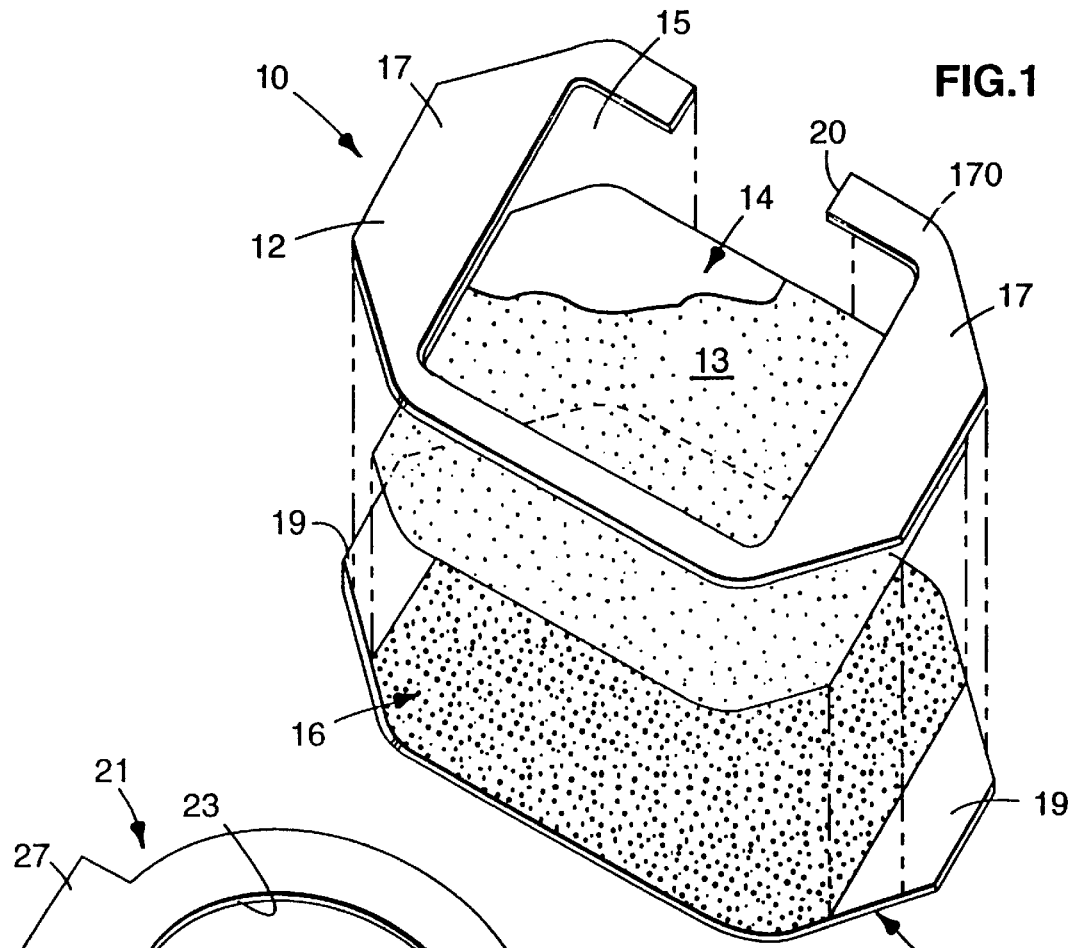
FIG. 1 is a top perspective view of one preferred embodiment of a dressing according to the present invention.
Figure 2A:
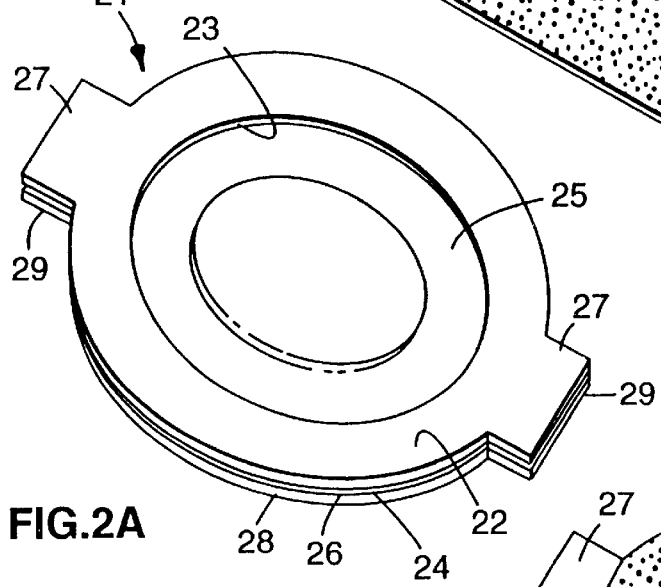
FIG. 2A is a top perspective view of an alternate preferred embodiment of a dressing according to the present invention.
Figure 2B:
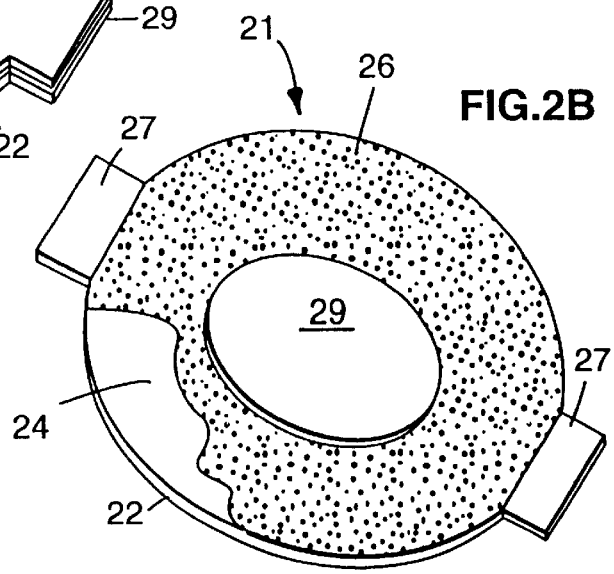
FIG. 2B is a bottom perspective view of the dressing of FIG. 2A with the liner removed.
Figure 3:
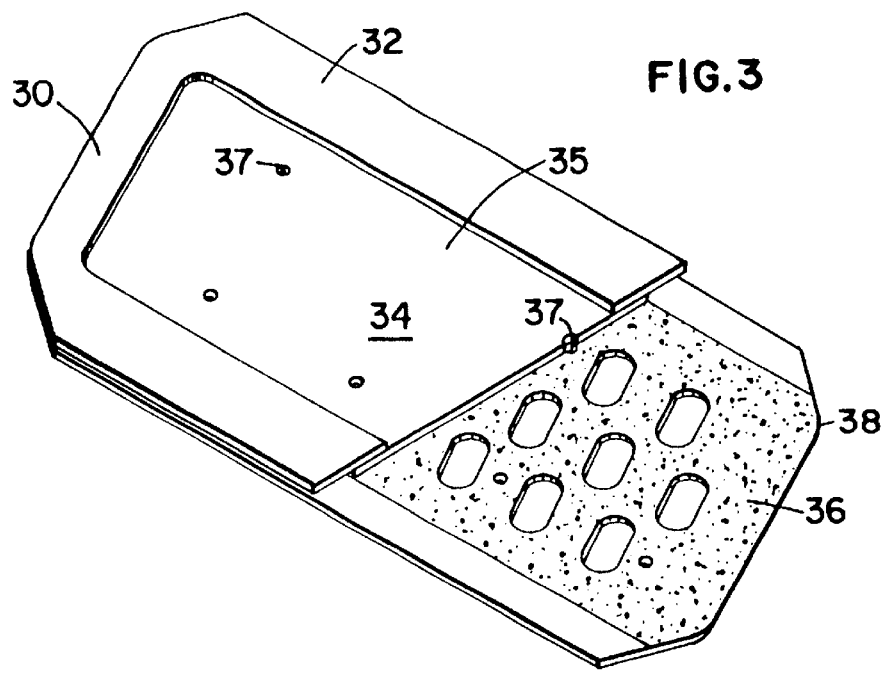
FIG. 3 is a top perspective view in partial cross-section of an alternate preferred embodiment of a dressing manufactured according to the present invention.

FIGS. 1–3 depict preferred embodiments of dressings manufactured according to the present invention. The adhesive composite configuration of the present invention is useful in connection with any conformable backing having a pressure-sensitive adhesive coating on it. Representative backings include nonwoven fibrous webs, woven fibrous webs, knits, films and other familiar backing materials. The preferred backing materials are translucent or transparent polymeric films.

The invention is particularly useful in the field of pressure sensitive adhesive composites having high moisture vapor permeable film backings. Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backing is preferably conformable to anatomical surfaces. As such, when the backing is applied to an anatomical surface, it conforms to the surface even when the surface is moved. The preferred backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

A description of this characteristic of backings preferred for use with the present invention can be found in issued U.S. Pat. Nos. 5,088,483 and 5,160,315, the disclosures of which are hereby incorporated by reference. As discussed, particularly preferred backings are elastomeric polyurethane, polyester, or polyether block amide films. These films combine the desirable properties of resiliency, high moisture vapor permeability, and transparency found in preferred backings.

The preferred pressure sensitive adhesives which can be used in the adhesive composites of the present invention are the normal adhesives which are applied to the skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl acrylate-:ethyleneoxide acrylate:acrylic acid terpolymer, as described in U.S. Pat. No. 4,373,410 (Example 31), the disclosure of which is hereby incorporated by reference. Other useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

The preferred pressure sensitive adhesives described above preferably transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001 which is hereby incorporated by reference.

Liners which are suitable for use in the adhesive composites of the present invention can be made of kraft papers, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference, describes low surface energy perfluorochemical liners. The preferred liners are papers, polyolefin films, or polyester films coated with silicone release materials. Examples of commercially available silicone coated release papers are POLYSLIK™ silicone release papers available from James River Co., H. P. Smith Division (Bedford Park, Ill.) and silicone release papers supplied by Daubert Chemical Co. (Dixon, Ill.). The most preferred liner is 1-60BKG-157 paper liner available from Daubert, which is a super calendared Kraft paper with a water-based silicone release surface.

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384–403. U.S. Pat. No. 4,472,480 also describes considerations pertinent to the selection of a perfluoropolyether release liner.

In the preferred embodiments according to the present invention, the choice of adhesives is limited to those that are safe to use on human skin, and preferably to those that are of the class known as "hypoallergenic". The preferred acrylate copolymers are adhesives of this class. Liners are available from a variety of manufacturers in a wide variety of proprietary formulations. Those skilled in the art will normally test those liners in simulated lose conditions against an adhesive of choice to arrive at a product with the desired release characteristics.

The carrier material used to supply the carriers for dressings manufactured according to the present invention is preferably substantially more rigid than the backing to prevent the backing from wrinkling during application. The carrier material must also be heat-sealable to the backing, with or without the low adhesion coating described below, for the purpose of manufacturing the preferred dressings. In general, the preferred carrier materials can include, but are not limited to, polyethylene/vinyl acetate copolymer-coated papers and polyester films. One example of a preferred carrier material is a polyethylene/vinyl acetate copolymer-coated super calendared Kraft paper (1-80BKG-157 PE; Daubert Chemical Co.).

The adhesive composites of the present invention preferably include a low adhesion coating on a top face of the backing, which is coated as a solution of polyvinyl N-octadecyl carbamate and a blend of silicone resins, further described in conjunction with Example 1 below. The preferred low adhesion coating is compatible with the heat seal bond between the carrier and the backing and also retains its low adhesion characteristics after heat sealing. While it is preferred that the top face of the adhesive composites of the present invention include a low adhesion coating, adhesive composites without such a coating with a carrier material heat sealed thereto are also considered to be within the present invention.

The preferred low adhesion coating, polyvinyl N-octadecyl carbamate, is disclosed in detail in U.S. Pat. No. 2,532,011, the disclosure of which is hereby incorporated by reference for its teaching relating to the manufacture and coating of low adhesion coatings. As described in that reference, the polyvinyl carbamate polymers which exhibit properties useful for the present invention have carbamate side chains terminating with an alkyl group more than five carbon atoms in length. They can be made by reacting polyvinyl alcohol and an appropriate isocyanate having a terminal alkyl group. In this regard, the preferred polyvinyl N-octadecyl carbamate is made by reacting polyvinyl alcohol and octadecyl isocyanate, which has 18 carbon atoms in the nitrogen-bonded side chain alkyl groups. As used here, the term "isocyanate" refers to monofunctional compounds containing a single ——N═══C═══O group, and does not include di-isocyanates.

It will also be understood that other coatings providing the low adhesion characteristics of the preferred coating could be substituted. The primary considerations in choosing any low adhesion coatings according to the present invention are their release characteristics and their compatibility with the heat seal bond between the carrier and the backing.

Because the low adhesion coating on the backing is very thin, the heat seal bond incorporates materials from all three layers of the carrier material, the low adhesion coating and the backing. As a result, the selection of the carrier material, low adhesion coating and backing must be made as a combination which provides suitable heat sealing characteristics. Examples of combinations providing suitable heat seal bonding are presented in the examples below, but it is contemplated that many other combinations will also satisfy the requirements for the apparatus and method according to the present invention.

Preferred Dressings

Turning to FIG. 1, one preferred embodiment of an adhesive composite dressing 10 comprises a backing 14 which is preferably conformable as described above; a low adhesion coating 13 on a top face of the backing 14; a carrier 170 attached to the top face of the backing 14 over the low adhesion coating 13; a pressure-sensitive adhesive 16 on a bottom face of the backing 14; and a liner 18 attached to the exposed surface of pressure-sensitive adhesive 16.

In the preferred embodiment, the carrier 170 is attached to backing 14 (over low adhesion coating 13) with a heat seal bond. In FIG. 1, a rectangular window portion cut in the carrier 170 is removed creating a frame 12 and a window 15 exposing a portion of the top face of the backing 14. Frame 12 provides rigidity to the backing 14 after liner 18 is removed. As described above, low adhesion coating 13 is compatible with the heat seal bond between the frame 12 and backing 14.

Liner 18 and frame 12 both preferably include tabs 17 and 19 which extend beyond the perimeter of backing 14 to provide a means of applying the backing/frame/adhesive composite without contacting the adhesive 16.

The heat seal bond between the carrier 170 and the backing 14 is stronger than the bond between the adhesive 16 and the liner 18. That difference ensures that the backing 14 remains attached to the frame 12 when liner 18 is removed from the adhesive composite dressing 10.

The dressing 10 is shown as having a frame 12 which includes an opening 20 such that the frame 12 does not extend completely around the perimeter of the backing 14. That feature allows the dressing 10 to be placed over catheters or other devices while still attached to the frame 12 to increase the ease of handling of backing 14.

In use, liner 18 is first removed from the adhesive composite dressing 10 leaving the frame 12/backing 14/pressure-sensitive adhesive 16 intact. The user can then manipulate the adhesive composite dressing 10 using tabs 17 on the frame 12 while viewing the area to which the dressing 10 will be attached through window 15 as the preferred backing 14 is transparent or translucent.

The removal of the window portion of the carrier material 170 which would normally cover window 15 is optional during manufacture. Removal does eliminate one step in the delivery process for previously known window style dressings (i.e., the step of removing a portion of the carrier material from the window 15 prior to removing the liner 18 from the remainder of the dressing 10) and reduces the waste stream at the consumer level. However, some customers prefer that the portion of the carrier 170 normally covering window 15 remains intact until the dressing reaches the end user.

In the preferred embodiments, the low adhesion coating 13 on the backing 14 also reduces dressing changes due to unwanted dressing removal when other tapes or devices are placed on the dressing 10 and removed. The low adhesion coating 13 also reduces the surface friction of the dressing 10 on linen or other fabrics, thereby offering additional protection against the accidental removal of dressings 10. In this regard, it will be appreciated that the unique features provided by a low adhesive coating on the backing 14, heat sealed under carrier 170, does not necessitate the removal of the carrier material from window 15 prior to use by the end user. However, the removal of such carrier material to expose window 15 during manufacture provides a means of making the adhesive composite dressings of the present invention.

Figure 10:
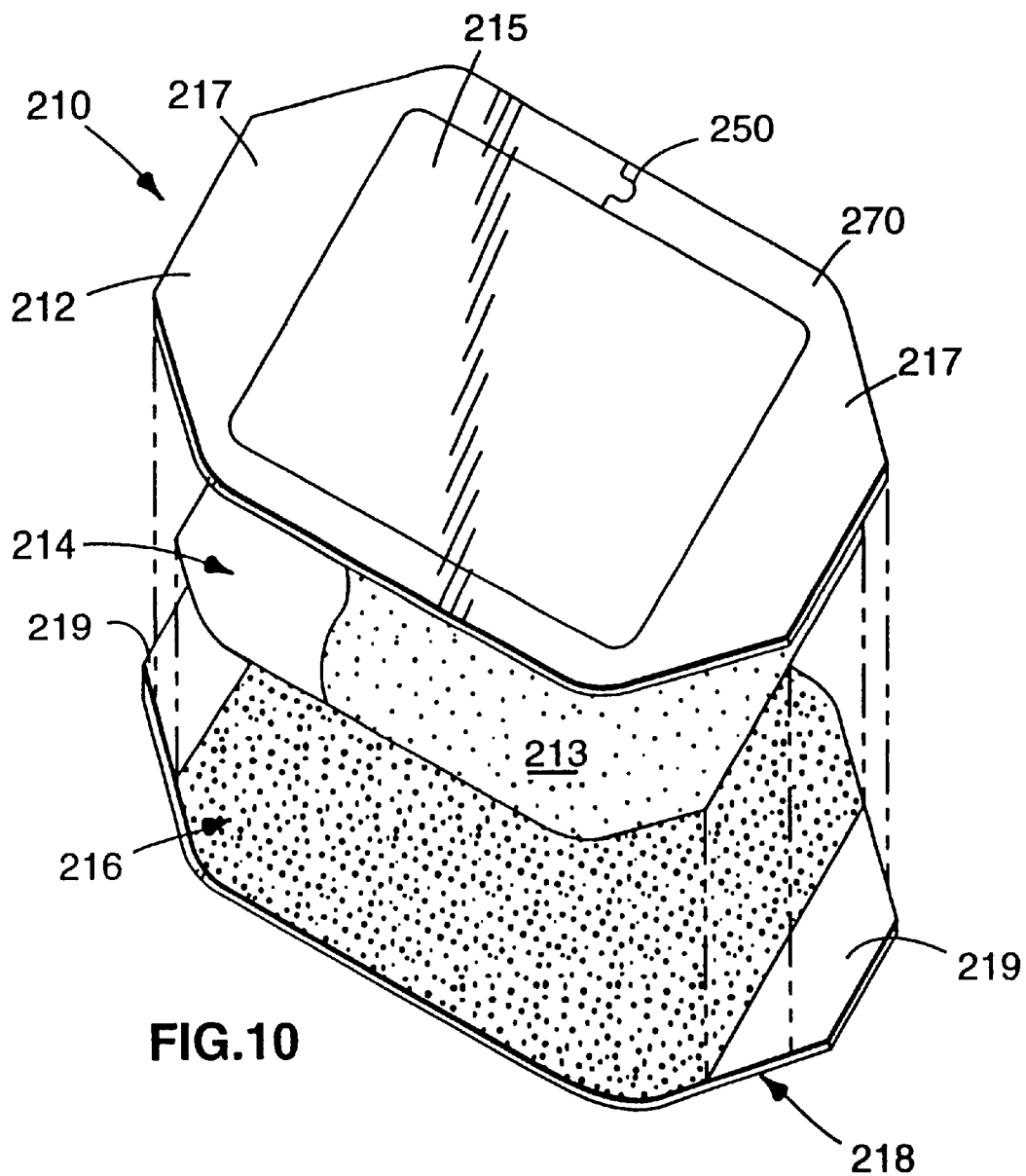
FIG. 10 is a top perspective view of an alternative preferred embodiment of a dressing according to the present invention.

FIG. 10 is an alternate embodiment of the present invention showing the window portion 215 cut within the carrier intact, i.e., not removed to expose a portion of the top face of the backing 214. The carrier 270 has a continuous periphery. Carrier 270 further includes a nonlinear cut 250. The cut provides a beginning point at which the frame 212 of the carrier 270 may be easily lifted from backing 214 and peeled. Although cut 250 may be a linear cut which is known in the art, the preferred embodiment includes a nonlinear cut. Nonlinear cuts provide more support for the backing 214 and frame 212 because nonlinear cuts are less likely to allow the frame 212 to fold at the cut line as compared to linear cuts which allow the frame to fold at the cut line. If frame 212 folds at the cut line 250, the backing 214 is likely to contact and the adhesive coated on the backing 214 will adhere to itself rendering the dressing 210 useless. A sinusoidal cut is shown in FIG. 10. However, any nonlinear cut including a zig zag or nonsymmetrical nonlinear cut would also provide sufficient support to the frame when placing the nonlinear cut would also provide sufficient support to the frame when placing the dressing.

Placing dressing 210 shown in FIG. 10 involves first removing the window portion 215 of the carrier 270. Liner 218 is then removed from the adhesive composite dressing 210 leaving the frame 212/backing 214/pressure sensitive adhesive 216 intact. By holding the dressing 210 at the tab portions 217, one may place the dressing 210 on a substrate by adhering the pressure sensitive adhesive 216/backing 214 composite to the area of the substrate which is viewed through the area of the backing 214 exposed by removal of carrier portion 215. The frame portion of the carrier 270 is then removed once the dressing 210 is adhered to a surface. Dressing 210 is shown with a single nonlinear cut 250 through the frame 212 portion of the carrier 270. Larger dressings, having larger carriers may employ more than one nonlinear cut 250 to more easily facilitate removal of the carrier 270 from the top of the backing 214.

Turning to FIGS. 2A and 2B, an alternate embodiment of a dressing 21 according to the present invention is depicted. As shown, the dressing 21 is an adhesive composite comprising a frame 22, a backing 24, adhesive 26 and a liner 28. Liner 28 preferably has opposing tabs 29 for handling, and frame 22 also includes tabs 27 for handling.

As with dressing 10 in FIG. 1, dressing 21 also includes an open area or window 25 in frame 22 which exposes a portion of the top surface of backing 24. Frame 22 preferably extends around the entire perimeter of backing 24 and preferably includes a control depth die cut 23 to facilitate removal of frame 22 from backing 24 after the dressing 21 has been applied to a patient.

FIG. 2B is a bottom view of dressing 21 with liner 28 removed to expose the adhesive layer 26 and absorbent pad 29 disposed proximate the center of the dressing 21. Absorbent pad 29 can be manufactured of a number of materials including, but not limited to, woven or nonwoven cotton or rayon. Absorbent pad 29 is useful for containing a number of substances, including antimicrobial agents, drugs for transdermal drug delivery, chemical indicators to monitor hormones or other substances in a patient, etc. Furthermore, although absorbent pad 29 is shown as centered on dressing 21, it can take any appropriate shape and/or can be located off-center on the dressing 21 as desired.

It should be noted that the removal by the manufacturer of the frame material 22 from the window area 25 of dressing 21 is advantageous with this embodiment of the present invention. Pad 29 tends to deform the backing 24 and cause delamination between the frame material 22 in window 25 if that material is still present when pad 29 is placed on dressing 21.

Turning to FIG. 3, another alternate preferred embodiment of a dressing 30 is depicted as manufactured according to the present invention. As shown there, the dressing 30 includes a carrier 32, backing material 34, adhesive 36 and liner 38. As with the embodiments described above, the carrier 32 is located around the perimeter of the backing 34 and a portion of the carrier is removed from the center 35 of the dressing 30 to provide a window and leaving a frame, exposing a portion of the top surface of backing 34 of the dressing 30.

This particular embodiment of the present invention is particularly useful for allergy testing as a patch testing system with the holes 37 used for the placement of allergens on a patient's skin for monitoring to determine whether an allergic reaction to that particular allergen occurs.

With larger dressings, such as those depicted in FIG. 3, multiple windows with supporting areas of carrier material in between each window (not shown) may be utilized to provide a more secure (e.g., rigid) means of delivery to a patient's skin. These supporting areas of carrier material help to insure that the dressings do not fold in and adhere to themselves during delivery. In addition, it will also be appreciated that any of the dressings of the present invention may include additional tape strips or other structures useful for securing devices (e.g., tubes, catheters) to a patient, as described in U.S. Pat. No. 5,160,315, the disclosure of which is herein incorporated by reference. The incorporation of these secural strips will be particularly useful in conjunction with a dressing including a low adhesion coating according to the present invention. In particular, a low adhesion coating on the top face of the backing will allow for the placement and replacement of such strips, thus obviating the need to replace the dressing when another secural configuration is desired.

Preferred Methods of Manufacture

Figure 4:
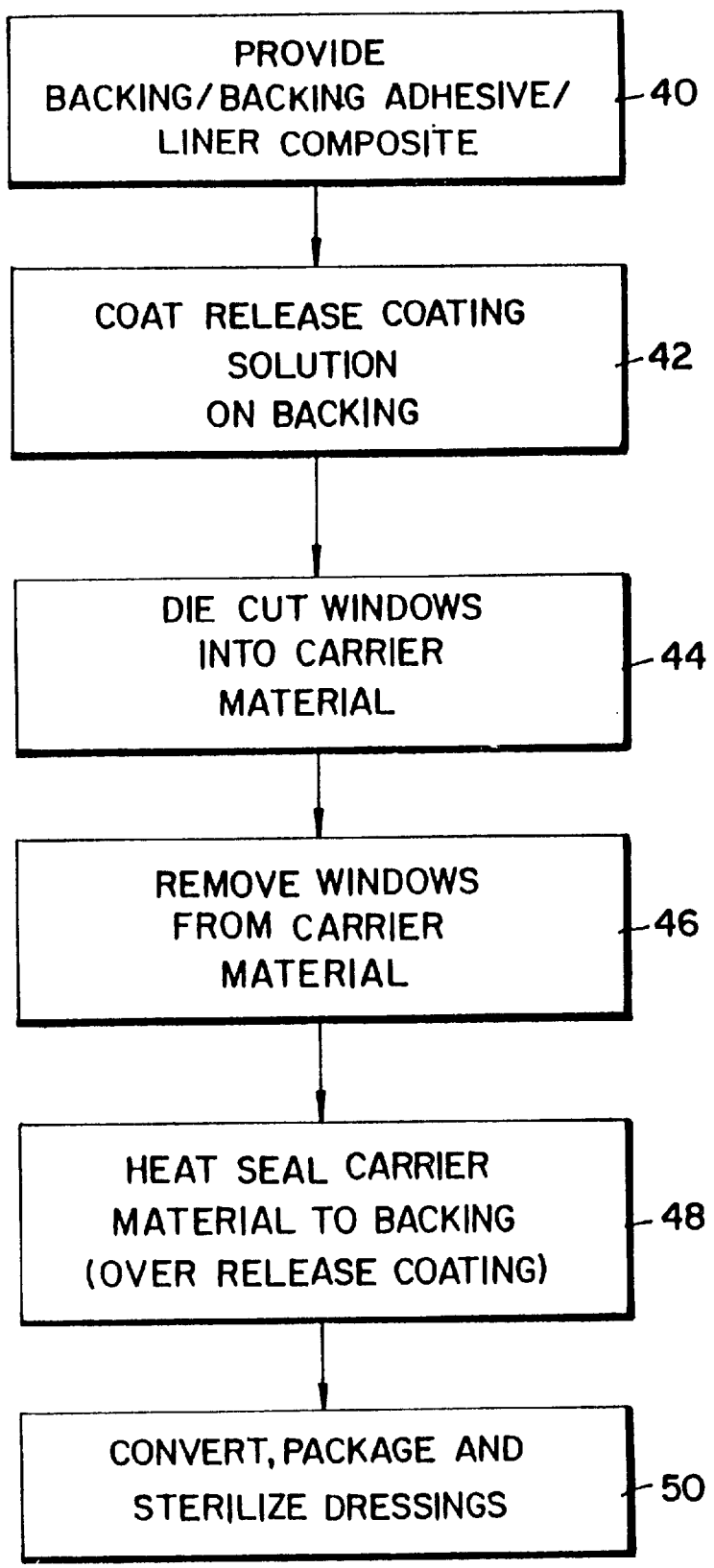
FIG. 4 is a flow chart of one preferred method of manufacturing dressings according to the present invention.

Turning now to the preferred and alternate methods of manufacturing dressings according to the present invention, the preferred basic method is depicted in the flowchart of FIG. 4. As shown there, step 40 preferably comprises providing an adhesive composite formed of a backing/ backing (pressure sensitive) adhesive/liner. The preferred materials for each component in that composite are described above.

Step 42 in the preferred method comprises providing a low adhesion coating on the top face of the backing to provide the tape-over feature, as well as to minimize surface friction due to linen which also reduces unwanted removal of the dressings.

In the preferred method, the carrier material is die cut 44 to form the windows which lie in the center of the carriers on the preferred dressings. In the preferred embodiments, the die cutting is accomplished using rotary die cutting equipment which is well known to those skilled in the art.

After the windows have been die cut in the carrier material, they are optionally removed in step 46. Removal of the windows defines the inner edge of the frame of carrier material which is located around the perimeter of each of the preferred dressings.

The windows die cut into the carrier material can be removed using a number of methods known to those skilled in the art. Those methods could include the use of vacuum, air pressure, gravity, and nip rolls having a small diameter which cause the windows to be removed from the framed carrier material.

As discussed above, the carrier material forming the window (which is removed) is preferably not heat sealed to the backing as is the remainder of the carrier material making up the frame of each dressing.

After the low adhesion coating step 42 and the die cutting 44 and window removal steps 46 are completed, the carrier material (with windows removed) is heat sealed 48 to the top face of the backing, over the low adhesion coating.

It will be understood that although steps 42, 44 and 46 are depicted sequentially in FIG. 4, they could be performed simultaneously and are shown sequentially only for convenience.

An alternate preferred method involves performing the heat sealing step 48 before the die cutting and window removal steps 44 and 46. In that method, the heat sealed areas preferably do not extend over the window areas on the backing to avoid heat sealing the window material to the backing, thereby making removal of the windows difficult. In addition, the die cutting step 44 now involves control depth die cutting to avoid cutting through the backing when the windows are cut out of the carrier material.

As stated above, it is desirable for the present invention that the bond between the carrier and the backing be more tenacious than the bond between the liner and the backing. Thus, the manufacturer must be able to exhibit control over the tenacity of the bonds. Heat sealing provides the manufacturer with increased control over the tenacity of the resulting bond as compared to extruding. Extruding involves spreading molten material over a substrate. To extrude, the material must obviously be heated to a temperature which causes the material to melt and become liquid. The manufacturer is therefore limited with regard to the minimum temperature which may be used to extrude a given material. Thus, a decreased temperature could not be used to limit the tenacity of an extruded bond. In contrast, heat sealing involves heating two materials and laminating the materials together. However, the materials do not need to be heated to a temperature which causes either of the materials to turn molten. The tenacity of a heat sealed bond is controlled by adjusting the temperature which the materials are heated and by adjusting the duration of the heating process. Since materials may be heat sealed, using greater temperature variability, heat sealing allows greater control over the tenacity of a bond as compared to extruding.

Additional control over the heat sealing process can be accomplished a number of ways. It can include cavities in the heated rolls used in heat sealing or other means, such as texturing the nip rolls which compress the adhesive composite web against the heated roll during processing. Those methods are described in greater detail below.

After the windows have been removed in steps 44 and 46 and the heat sealing step 48 has been performed, the only remaining step 50 is to convert the adhesive composite web into finished product. In the preferred methods, the web now consists of the frame material heat sealed to the backing which has an adhesive and liner on its opposing side. In addition, the windows defining the center of each dressing have been removed from the carrier material. That web is preferably directed into a rotary die sheeting station which cuts the dressings out of the web and pulls the weed or waste material away for disposal. Preferably, the individual dressings are fed directly into a packaging station which packages the dressings for sterilization and delivery to customers.

Figure 5A:
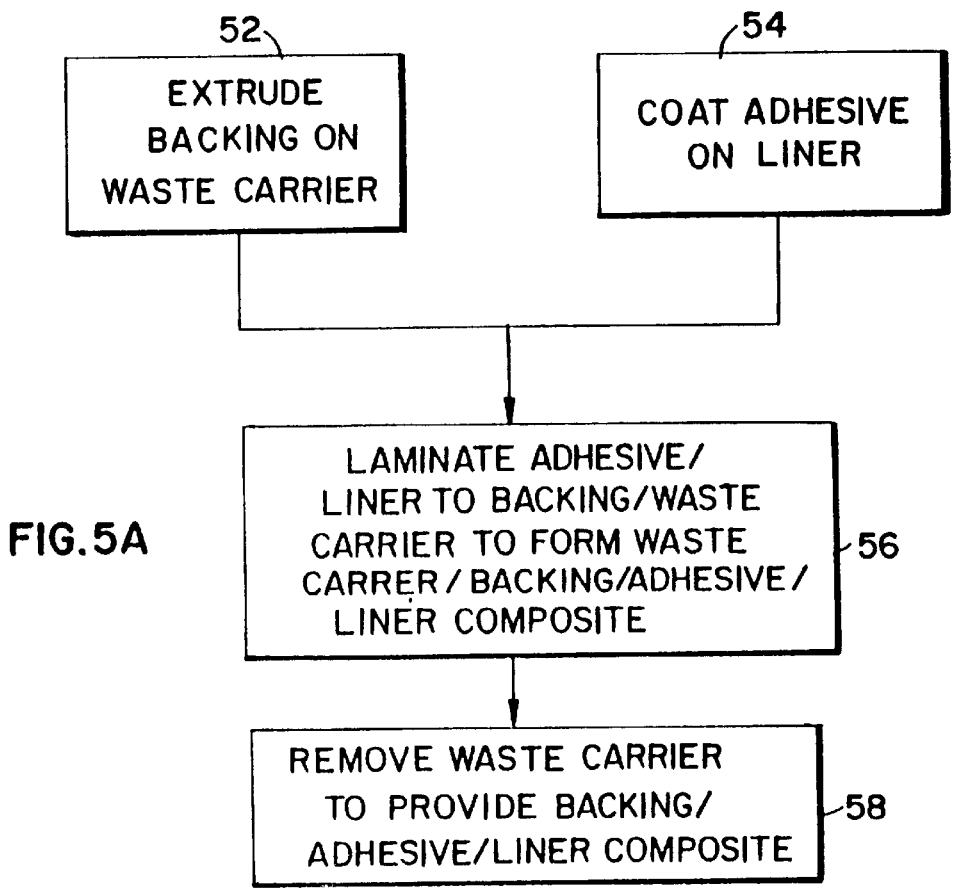

FIGS. 5A and 5B depict two alternate preferred methods of accomplishing step 40, i.e., providing the backing/ backing (pressure sensitive) adhesive/liner composite used in step 40 described above. FIG. 5A depicts one method including step 52 which comprises the extrusion or coating of the backing on a waste carrier material. Step 54 comprises the coating of the backing adhesive on the liner to form a backing adhesive/liner composite. The backing adhesive/liner composite is laminated to the backing/waste carrier composite in step 56 to form a waste carrier/backing/backing adhesive/liner composite. Finally, the waste carrier is removed from the backing to provide a composite comprising the backing/backing (pressure sensitive) adhesive/liner composite material which can then be processed as described in the method of FIG. 4.

Turning to FIG. 5B, in an alternative embodiment, the backing adhesive is coated on the liner in step 60 and in step 62 the backing material is extruded or coated directly onto the pressure sensitive adhesive to provide a backing/backing (pressure sensitive) adhesive/liner composite material. The method described in FIG. 5B is somewhat advantageous over that described in FIG. 5A as it avoids the use of a waste carrier to reduce product costs and processing steps. Both methods are, however, contemplated for use in the methods according to the present invention.

FIGS. 6–9 depict various schematic diagrams of web fed rotary processing equipment for producing dressings according to the preferred methods of the present invention. The details of designing such equipment will be well known to those skilled in the art. Commercially available rotary web processing equipment including control depth die cut systems useful for practicing the method of the present invention can be obtained from, for example, the Mark Andy Company (St. Louis, Mo.) and Bernal Rotary Systems (Troy, Mich.).

Turning to FIG. 6, roll 72 preferably comprises a heat sealable carrier material (also designated 72) as described above with the heat seal side 73 threaded as shown. The carrier material 72 is wrapped around a heated roll 82 as shown. The second input roll 70 comprises the low adhesion coating/backing/backing (pressure sensitive) adhesive/liner composite (also 70) according to the present invention. The low adhesion coating/backing portion 74 is wound in and the liner 78 is wound out as shown. The web from input roll 70 is threaded between the nip 81 formed between nip roll 80 and heated roll 82. In the preferred embodiment as shown, heated roll 82 includes cavities 83 disposed around its perimeter which are provided to avoid heat sealing areas 84 in the web as it exits the heated roll nip 81.

Downstream, die cut roll 86 and anvil roll 87 control depth die cut the carrier material 72 to form windows in the web. The windows 88 are then optionally removed using a variety of means as discussed above. Pull rolls 90 establish a constant tension zone and sheeting rolls 92 remove the finished product 10 from the web. Weed 94 is wound on roll 96 and is then disposed.

Figure 7:
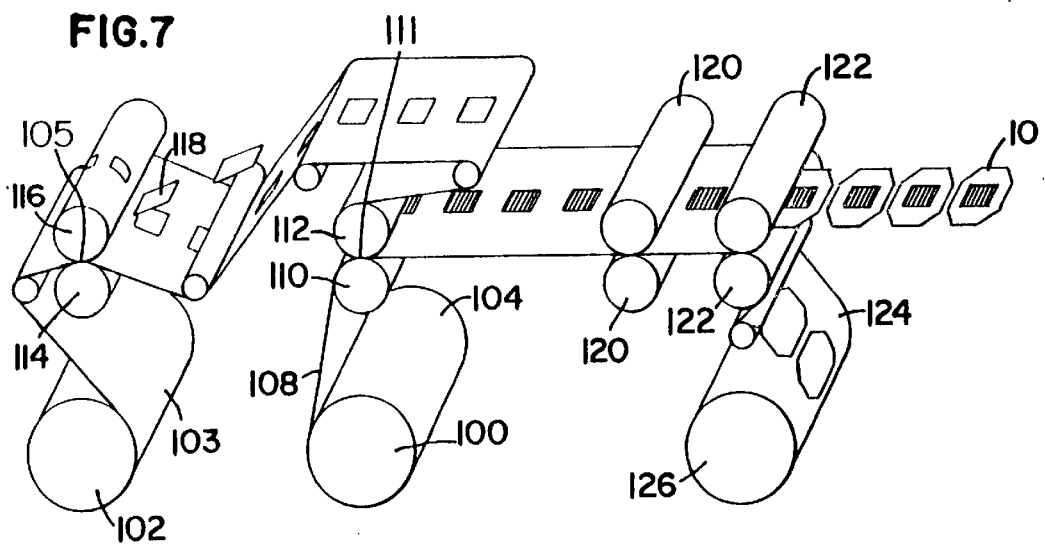
FIG. 7 is a schematic diagram in perspective of an alternate preferred method of manufacturing dressings according to the present invention.

In an alternative embodiment illustrated in FIG. 7, the carrier material roll 102 is provided with its heat sealable side 103 wound out. The carrier material (also 102) is threaded through a nip 105 formed between a die cut roll 116 and anvil roll 114. At that station the windows 118 are cut from and removed from the web of carrier material 102.

Carrier material 102 is threaded through the lamination nip 111 formed by heated roll 112 and nip roll 110 as shown. Also threaded into that lamination station is the low adhesion coating/backing/backing (pressure sensitive) adhesive/liner composite of the present invention off of feed roll 100 with the low adhesion coating/backing portion 104 wound out and the liner 108 wound in as shown. In the embodiment pictured in FIG. 7, heated roll 112 does not need cavities as described with respect to heated roll 82 in FIG. 6 because the window material in carrier 102 is removed prior to the heat laminating step. Pull rolls 120 establish a constant tension zone for sheeting dies 122 which produce dressings 10 and weed 124 which is wound on roll 126.

Figure 8:
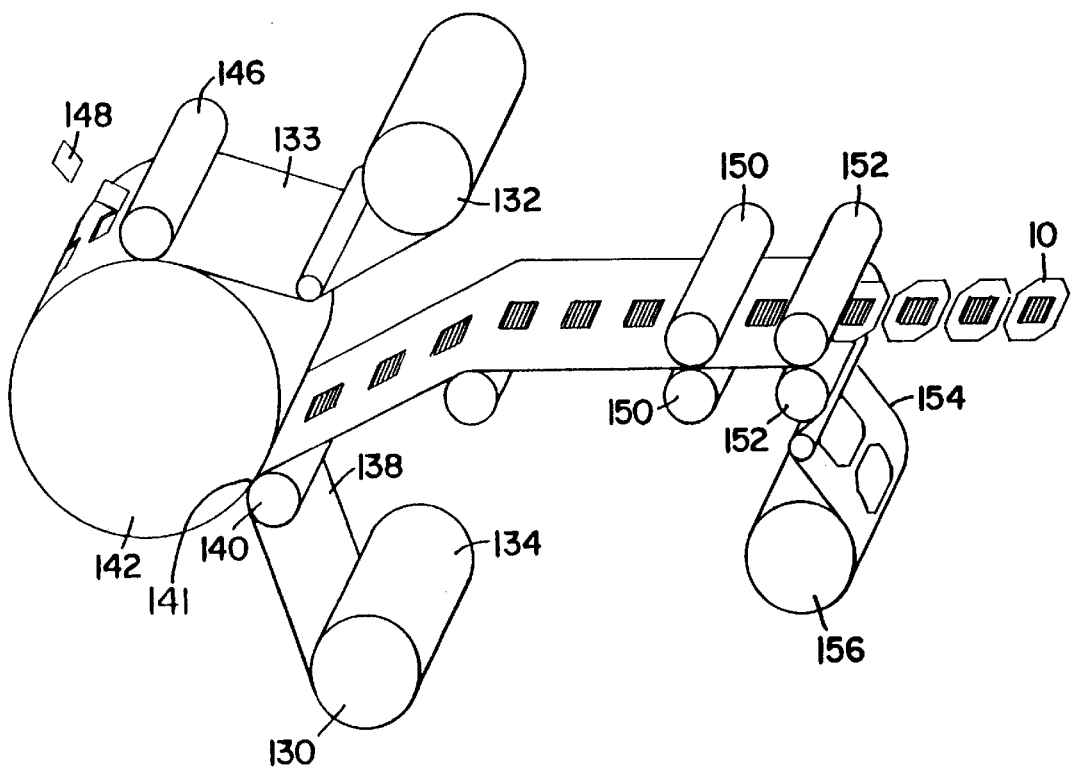
FIG. 8 is a schematic diagram in perspective of an alternate preferred method of manufacturing dressings according to the present invention.

Turning to FIG. 8, which illustrates another alternative method, the carrier material 132 is supplied with the heat sealable side 133 threaded in as shown. In this process, the control depth die cutting is performed at the same station as the heat lamination. Roll 142 is the heated roll and 146 is the die cut roll which produces the window materials 148 which are removed from the carrier material 132.

The low adhesion coating/backing/backing (pressure sensitive) adhesive/liner composite 130 is wound into the nip 141 formed between roll 140 and heated roll 142. Composite 130 is preferably wound with the low adhesion coating/backing portion 134 out and the liner 138 wound in. After the carrier 132 and composite 130 have been laminated together they are fed into pull rolls 150 which provide a constant tension zone for sheeting dies 152 which produce dressings 10 and waste or weed 154 which is wound on roll 156.

Figure 9:
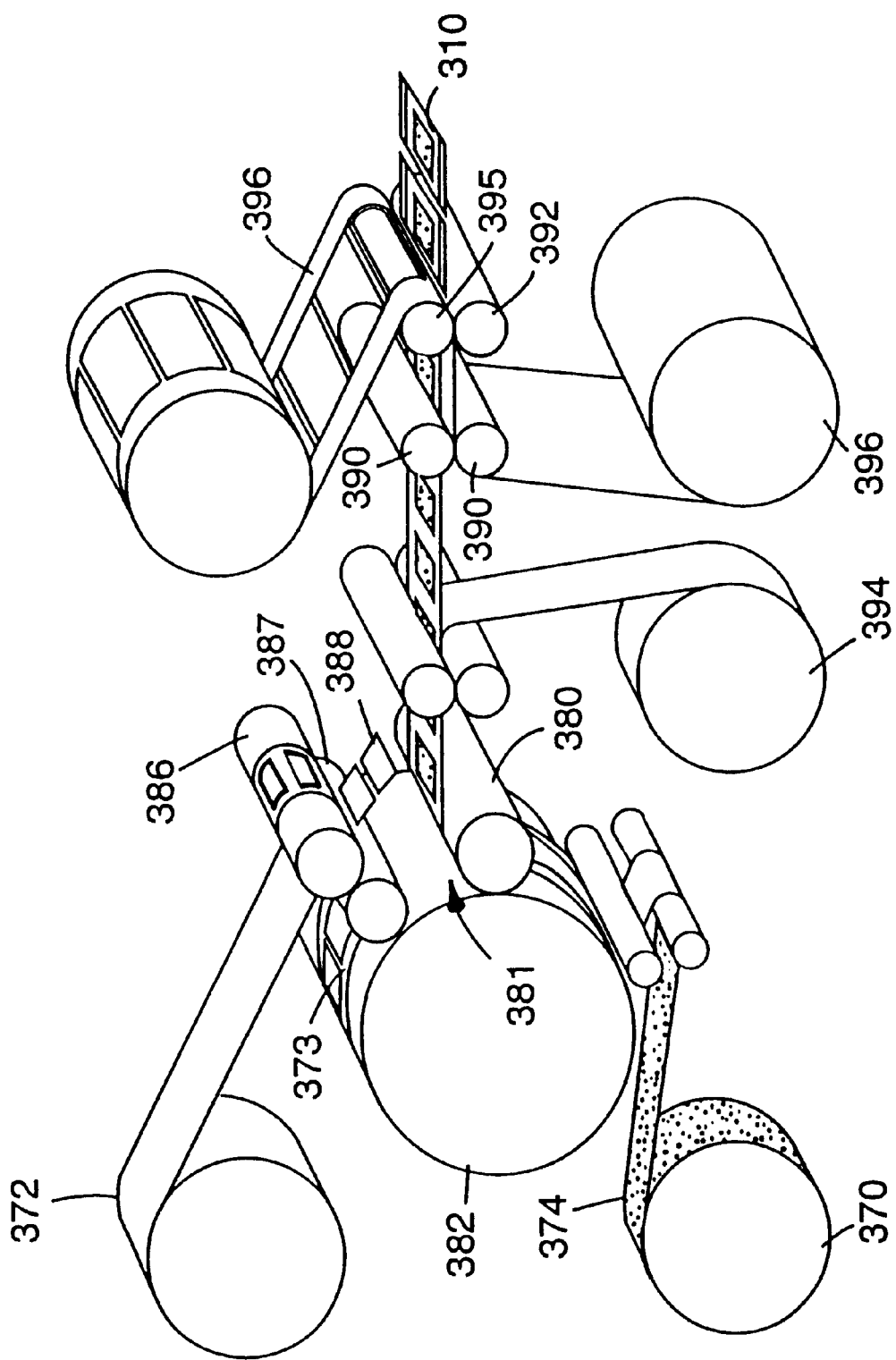
FIG. 9 is a schematic diagram in perspective of an alternate preferred method of manufacturing dressings according to the present invention.

Turning to FIG. 9, roll 372 preferably comprises a heat sealable carrier material (also designated 372) as described above with the heat seal side 373 threaded as shown. The carrier material 372 is threaded between anvil roll 387 and a die cut roll 386. The die cut roll 386 and the anvil roll 387 die cut the carrier to form windows in the carrier material 372. The windows 388 are then removed using a variety of means as discussed above. The carrier material 372 is then rolled around a heated roll 382.

The second input roll 370 comprises the film/adhesive/waste liner composite (also designated 370) according to the present invention. The film portion 374 is wound in and the liner 378 is wound out as shown. The web from input roll 370 is threaded between the nip 381 formed between the nip roll 380 and heated roll 382. Roll 394 removes waste liner (also designated 394) from the film/adhesive 370 composite allowing the product liner 396 (also on roll 396) to be laminated to the adhesive of composite 370 at the nip formed between rolls 390. After the liner 396 and the composite 370 have been laminated together, they are fed into a nip created by anvil roll 392 and product die roll 395. Weed 396 is wound on the weed roll (also designated 396) and is then disposed. The finished product 310 is released from the nip created by anvil roll 392 and die roll 395.

It will be understood by those skilled in the art that the schematic diagrams contained in FIGS. 6–9 represent possible equipment configurations only and should not be construed as limiting the method of the present invention.

The heat seal portion of the methods according to the present invention must be carefully controlled because of the importance of the relative strength of the heat seal bond between the backing and the frame material (over the low adhesion coating) as compared to the bond between a patient's skin and the backing adhesive. As discussed above, the heat seal bond between the frame and backing must be stronger than the bond between the backing adhesive and the liner. That relationship prevents delamination of the frame from the backing when the liner is removed before applying the dressing to a patient.

Also, it is preferred that the carrier material in the window, which is removed either by the manufacturer or by the consumer, is not heat sealed to the backing because of the difficulty associated with removing the window if it is heat sealed to the backing. Alternatively, if the window material is heat sealed to the backing, it is preferred that the strength of that heat seal bond is less than the strength of the heat seal bond between the carrier and backing to facilitate removal of the windows without adversely affecting the bond between the frame and backing.

It will be understood that control over the bonds produced during the heat seal portion of the manufacturing is affected by a number of variables including the materials heat sealed, the temperature of the heated roll, the speed of the web and pressure between the heated roll and a nip roll.

Furthermore, it will be understood that sterilization of the resulting products can also affect the bond strength. In particular, it is known that the strength of the bond between the preferred backing adhesive and a patient's skin is affected by gamma sterilization. Gamma sterilization also has been found to have some effect in strengthening heat seal bonds produced using the present invention, but the effect is much less pronounced than the effect on the backing adhesive/skin bond strength.

Variations in the heated roll to control the areas bonded by the heat seal process described above include the formation of cavities in the heated roll, or alternatively the nip roll, to produce areas in which little or no heat seal bond is produced (See e.g., FIG. 6, roll 82 with cavity 83 and unbonded area 84 in the web). FIGS. 7, 8 and 9 depict processes in which the window materials are removed before heat sealing to avoid the problem of controlling the heat sealing in the window area (see FIG. 7, windows 118; FIG. 8, windows 148 and FIG. 9, windows 388).

Another method to control heat sealing of the carrier to the backing is the use of a textured nip roll in conjunction with the heated rolls as described above. The texturing can be useful to control the area under compression between the nip roll and the heated roll, as well as having an effect on the overall compressive force between the rolls. The texturing could cover the entire surface of the roll, or be limited to areas on the roll which correspond to areas on the web in which the bond strength is preferred to be stronger or weaker.

The texturing could take many forms, including, but not limited to, as parallel or intersecting grooves at any suitable angle with respect to the centerline of the web or a knurled pattern formed in the roll. The primary consideration is to reduce or control the area of contact between the nip roll and the heated roll, thereby controlling the bond strength.

The preferred textured nip roll has a pattern of intersecting grooves milled in a silicone coated roll with a durometer of about 85 Shore A hardness. The grooves are set at angles of approximately 45 degrees from the machine direction along the face of the roll. When not compressed, the grooves reduce the contact surface of the nip roll by about 50%.

Alternatively, it will be understood that the heated roll could be textured to provide additional control over the heat sealing process.

Another variation to provide control over the heat seal bonds is the use of elastomeric nip rolls formed of materials with varying durometers to provide different compression ratios across the nip area, thereby affecting the heat seal bond strength. This particular variation relies on varying the compressive forces to control bond strength and, in some instances, could be used in conjunction with texturing.

The following non-limiting examples will further illustrate the articles and methods of the present invention. All parts and percentages are expressed as parts by weight unless otherwise indicated.

EXAMPLE 1

Twenty-five grams per square meter of a pressure sensitive adhesive prepared in accordance with U.S. Pat. No. Re. 24,906, comprising a copolymer of 96% units of isooctyl acrylate and 4% units acrylamide was applied to a 78 pound bleached release liner, one side coated, polyethylene and silicone paper (POLYSLIK S-8053, H. P. Smith, Chicago, Ill.) using a standard horizontal knife coater.

A 1.1 mil (28 micron) film of ESTANE 58309NAT022 polyurethane resin (B. F. Goodrich, Cleveland, Ohio) was laminated to the adhesive surface to form the backing for the dressings. At that point, the backing/backing (pressure sensitive) adhesive/liner composite was completed.

The next step was to coat a low adhesion layer on the backing to provide the tape-over feature of the present invention. Using a Gravure station, a 6% solids solution (20 parts silicone and 80 parts polyvinyl N-octadecyl carbamate) was coated on the polyurethane (non-adhesive) side of the composite using a 200 line pyramid knurl and dried. The solution comprised:

1) a silicone resin blend of SS4300 at 95% units and SR-0545 at 5% units, both from General Electric (Waterford, N.Y.) provided in 90% toluene (by weight); and 2) a backsizing solution in accordance with U.S. Pat. No. 2,532,011, comprising polyvinyl N-octadecyl carbamate 5% solids in xylene-toluene (22%–78% by weight).

The low adhesion coating/backing/backing (pressure sensitive) adhesive/liner composite web was then slit to proper width to make the size dressing desired.

A carrier material (1-80BKG-157 & PE; Daubert Chemical Co.) was then die cut, to form windows which were then removed.

The PE side of the carrier material was heat laminated to the backing (over the low adhesion coating) of the above composite. The POLYSLIK S-8053 was removed and replaced with a wider liner (2-60BKG-157-99AM; Daubert Chemical Co.) sheeted to the proper dressing size using rotary equipment similar to die-cutting/printing machines manufactured by Mark Andy (St. Louis, Mo.). The station modified for heat sealing used a heated roll manufactured by Tokuden Ltd. (Kyoto, Japan).

EXAMPLE 2

The procedure of Example 1 was followed except that the carrier material (1-80BKG-157 and PE) was die cut with a window and then the slug removed after heat sealing and liner swap. In this case the Tokuden heated roll was milled to form cavities that would not seal in the window portion.

EXAMPLE 3

The procedure of Example 1 was followed except that the low adhesion coating was left off the backing, thereby illustrating that the adhesive composites of the present invention can be made without a low adhesion coating on the top of the backing. In this regard, the peel force of the bond between the carrier material and the film backing was compared between the low adhesion coated composite of Example 1 and the uncoated composite of Example 3 using the following procedure.

The peel force of each composite was measured using a 90 degree rotary peel adhesion test on an Instron testing machine (Model No. 1122; Instron Corp., Canton, Mass.). A 2.54 cm wide double coated tape was adhered to the full circumference of a rotatable metal wheel which was mounted on the lower jaw of the Instron machine. A 2.54 cm wide polyester silicone adhesive tape (No. 8402 tape, 3M Company, St. Paul, Minn.) was adhered to the double coated tape, adhesive side out. The sample composite dressings were die cut into 2.54 cm×10.2 cm strips, each of which was placed on the silicone tape covering the wheel with the carrier material facing against the wheel and the pressure sensitive adhesive surface facing the operator. Prior to testing, one end of the film/adhesive portion of the sample strip was lifted away from the carrier to form a tab, which was clamped onto the upper jaw of the Instron machine. The film/adhesive composite was then peeled off the carrier material at a 90 degree angle and crosshead speed of 300 mm/min. The peel force was recorded in grams force per 2.54 cm width.

Samples of both Example 1 and Example 3 composites were tested using the procedure described above. One skilled in the art would recognize that line speed, nip temperature and materials selections are the three main variables to consider when laminating materials together. Other variables investigated include web tension, nip pressure, and the durometer of the rubber roll used at the heated lamination station. The effect of these variables proved to be significant. In this regard, the affect of manufacturing line speed (meters/min) and heat seal temperature (° C.) on the peel force (g/2.54 cm width) between the carrier material and film backings of the dressing composites of Examples 1 and 3 are shown below in Table 1.

TABLE 1

Effect of manufacturing line speed and heat seal temperature on the peel force between the carrier material and film backings of the dressing composites of Examples 1 and 3.

| Example Number | line speed (m/min) | heat seal temperature (° C.) | peel force (g/2.54 cm width) |
|---|---|---|---|
| 1 | 1.5 | 93 | 65 |
| 1 | 1.5 | 116 | 113 |
| 1 | 10.7 | 93 | 29 |
| 1 | 10.7 | 116 | 48 |
| 3 | 1.5 | 93 | 76 |
| 3 | 1.5 | 116 | 142 |
| 3 | 10.7 | 93 | 10 |
| 3 | 10.7 | 116 | 46 |

Surprisingly, the heat seal bond force between the carrier material and film backing of the composite dressings of Example 1 was comparable with bond force for the composites of Example 3, despite the fact that the backing of the Example 1 composites were coated with a low adhesion coating prior to heat sealing. In fact, at high line speeds and lower heal seal temperatures, these low adhesion coating containing composites exhibited superior bond force to the composites of Example 3, which did not contain a low adhesion coating in between the backing and carrier material.

EXAMPLE 4

The procedure of Example 1 was followed except a PE-44 polyurethane resin (Morten International, Seabrook, N.H.) was extruded with a thickness of 1.1 mil (28 micron) directly to the pressure sensitive adhesive coated on the high release side (i.e. side 99AM) of the preferred liner (2-60BKG-157-99AM; Daubert Chemical Co.). The coating solution was comprised of a copolymer of 70% monomeric units of isooctyl acrylate, 15% monomeric units of ethyleneoxide acrylate and 15% monomeric units of acrylic acid and was coated at a coating weight of thirty grams per square meter.

EXAMPLE 5

The film backing and adhesive construction of Example 4 were used in conjunction with a carrier material SCOTCHPAK® 1220 film—a clear, heat-sealable polyester film laminate (3M Company, St. Paul, Minn.), and was formed using the same procedures and equipment as used in Example 1 herein.

EXAMPLE 6

The protocol of Example 1 was followed except that the carrier material was control depth die cut to the film after placing the 2-60BKG-157-99AM liner. The carrier inside the die cut (window) was left in place for Example 6 as compared to Example 1 where it was removed.

In view of the foregoing description, it will be apparent that the methods and composite dressings of the invention are not limited to the specific details set forth herein for purposes of illustration, and that various other modifications are equivalent for the stated and illustrated functions without departing from the spirit of the invention and the scope thereof as defined in the appended claims.

What is claimed is:

1. An adhesive composite dressing comprising:
   (a) a conformable backing having top and bottom faces, the backing comprising a polymer film;
   (b) a pressure sensitive adhesive coated on at least a portion of the bottom face of the backing;
   (c) a liner releaseably adhered to the pressure sensitive adhesive opposite the backing; and
   (d) a carrier releasably heat-sealed to the polymer film with a heat seal bond, the carrier substantially defining a window proximate a center of the backing and a carrier frame proximate a perimeter of the backing, the carrier further being formed of material substantially more rigid than the polymer film to provide rigidity to the backing and the pressure sensitive adhesive after removal of the liner.

2. The adhesive composite dressing of claim 1, wherein the backing further comprises a multi-layer composite.

3. The adhesive composite dressing of claim 2, wherein a layer of the backing comprises an absorbent material.

4. The adhesive composite dressing of claim 3, wherein the absorbent material contains one or more substances selected from the group consisting of antimicrobial agents, drugs, chemical indicators, and combinations thereof.

5. The adhesive composite dressing of claim 1, wherein the heat seal bond between the carrier and the polymer film is stronger than the bond between the pressure sensitive adhesive and the liner.

6. The adhesive composite dressing of claim 1, wherein the polymer film of the backing is selected from the group consisting of polyurethane film, polyester film, polyether block amide film, and combinations thereof.

7. The adhesive composite dressing of claim 1, wherein the backing and pressure sensitive adhesive transmit moisture vapor at a rate of at least 300 g/m$^2$/24 hrs/37° C./100-10% RH.

8. The adhesive composite dressing of claim 1, wherein the top face of the backing within the window defined by the carrier is exposed.

9. An adhesive composite dressing comprising:
   (a) a conformable backing having top and bottom faces, the backing comprising a polymer film;
   (b) a pressure sensitive adhesive coated on at least a portion of the bottom face of the backing;

(c) a liner releaseably adhered to the pressure sensitive adhesive opposite the backing; and (d) a carrier releasably heat-sealed to the polymer film with a heat seal bond, the carrier substantially defining a window proximate a center of the backing and a carrier frame proximate a perimeter of the backing, the carrier further being formed of material substantially more rigid than the polymer film to provide rigidity to the backing and the pressure sensitive adhesive after removal of the liner, wherein the heat seal bond between the carrier and the polymer film is stronger than the bond between the pressure sensitive adhesive and the liner, and further wherein the top face of the backing within the window defined by the carrier is exposed.

10. The adhesive composite dressing of claim 9, wherein the polymer film of the backing is selected from the group consisting of polyurethane film, polyester film, polyether block amide film, and combinations thereof.

11. The adhesive composite dressing of claim 9, wherein the backing and pressure sensitive adhesive transmit moisture vapor at a rate of at least 300 g/m$^2$/24 hrs/37° C./100-10% RH.

* * * * *